US007696259B2

(12) United States Patent
Hanley et al.

(10) Patent No.: US 7,696,259 B2
(45) Date of Patent: Apr. 13, 2010

(54) COATING FOR BIOMEDICAL DEVICES

(75) Inventors: Patrick Hanley, Barna (IE); Finbar Dolan, Moate (IE); Clement Higginbotham, Athlone (IE); Morgan Tierney, Ferbane (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/553,546

(22) PCT Filed: Apr. 16, 2004

(86) PCT No.: PCT/IE2004/000057

§ 371 (c)(1),
(2), (4) Date: Sep. 12, 2006

(87) PCT Pub. No.: WO2004/091685

PCT Pub. Date: Oct. 28, 2004

(65) Prior Publication Data

US 2007/0043160 A1   Feb. 22, 2007

(30) Foreign Application Priority Data

Apr. 17, 2003 (IE) .............................. S2003/0294

(51) Int. Cl.
C08J 3/28 (2006.01)
(52) U.S. Cl. .................. 522/144; 522/40; 522/109; 522/120; 522/121; 522/142; 427/487; 427/508; 427/520
(58) Field of Classification Search .................. 522/40, 522/109, 114, 120, 121, 142; 427/487, 508, 427/520
See application file for complete search history.

(56) References Cited

U.S. PATENT DOCUMENTS

| 4,100,309 | A | 7/1978 | Micklus et al. |
| 4,156,067 | A | 5/1979 | Gould |
| 4,255,550 | A | 3/1981 | Gould |
| 4,373,009 | A | 2/1983 | Winn |
| 4,472,467 | A | 9/1984 | Tamaki et al. |
| 4,496,535 | A | 1/1985 | Gould et al. |
| 4,550,126 | A | 10/1985 | Lorenz |
| 4,572,833 | A | 2/1986 | Pedersen et al. |
| 4,589,873 | A | 5/1986 | Schwartz et al. |
| 4,642,267 | A | 2/1987 | Creasy et al. |
| 4,769,013 | A | 9/1988 | Lorenz et al. |
| 4,835,003 | A | 5/1989 | Becker et al. |
| 4,973,493 | A | 11/1990 | Guire |
| 4,979,959 | A | 12/1990 | Guire |
| 5,001,009 | A | 3/1991 | Whitbourne |
| 5,002,582 | A | 3/1991 | Guire et al. |
| 5,005,287 | A | 4/1991 | Ritter |
| 5,026,607 | A | 6/1991 | Kiezulas |
| 5,061,424 | A | 10/1991 | Karimi et al. |
| 5,290,585 | A | 3/1994 | Elton |
| 5,331,027 | A | 7/1994 | Whitbourne |
| 5,414,075 | A | 5/1995 | Swan et al. |
| 5,443,907 | A | 8/1995 | Slaiken et al. |
| 5,509,899 | A | 4/1996 | Fan et al. |
| 5,525,348 | A | 6/1996 | Whitbourne et al. |
| 5,531,715 | A | 7/1996 | Engelson et al. |
| 5,599,352 | A | 2/1997 | Dinh et al. |
| 5,620,738 | A | 4/1997 | Fan et al. |
| 5,652,347 | A | 7/1997 | Pouyani et al. |
| 5,665,840 | A | 9/1997 | Pohlmann et al. |
| 5,702,754 | A | 12/1997 | Zhong |
| 5,776,611 | A | 7/1998 | Elton et al. |
| 5,824,048 | A | 10/1998 | Tuch |
| 5,853,745 | A | 12/1998 | Darouiche |
| 5,869,127 | A | 2/1999 | Zhong |
| 6,077,698 | A | 6/2000 | Swan et al. |
| 6,107,361 | A * | 8/2000 | Tortorello et al. ............. 522/96 |
| 6,110,483 | A | 8/2000 | Whitbourne et al. |
| 6,162,511 | A * | 12/2000 | Garnett et al. ............. 427/514 |
| 6,340,465 | B1 | 1/2002 | Hsu et al. |
| 6,558,799 | B2 * | 5/2003 | Takeuchi et al. ......... 428/423.1 |
| 6,706,408 | B2 * | 3/2004 | Jelle .......................... 428/447 |
| 6,737,122 | B2 * | 5/2004 | Beck et al. ................. 427/492 |
| 6,835,759 | B2 * | 12/2004 | Bradford et al. ............ 522/104 |

FOREIGN PATENT DOCUMENTS

| WO | WO 98/58988 | | 12/1998 |
| WO | WO 00/30696 | | 6/2000 |
| WO | WO 01/17575 | | 3/2001 |
| WO | WO02/48202 | * | 6/2002 |

OTHER PUBLICATIONS

Fujimoto et al., J. Polymer Science, Polymer Chemistry Edition, (1993), 31, pp. 1035-1043.
Amiji & Park, ACS Symp. Ser (1994), 540, pp. 135-146.
Freij-Larsson & Wessien, Journal of Applied Polymer Sciences, (1993), 50, pp. 345-352.
Y. Uyama & Y. Ikada, "Graft Polymerization of Acrylamide onto UV-Irradiated Films," Journal of Applied Polymer Science, vol. 36, 1087-1096 (1988).
Ruckert & Geuskens, "Surface Modification of Polymers—IV. Grafting of Acrylamide Via an Unexpected Mechanism Using a Water Soluble Photo-Initiator," Eur. Polym. Journal, vol. 32, No. 2, pp. 201-208 (1996).

(Continued)

Primary Examiner—Helen L. Pezzuto

(57) ABSTRACT

A coating formulation for a substrate having abstractable hydrogen radicals is disclosed. The formulation includes a hydrophilic polymeric component comprising at least two polymeric species of differing molecular weights, an unsaturated hydrophilic monomer capable of free-radical polymerisation in the presence of a radical and a UV activatable compound capable of abstracting hydrogen radicals from the surface to be coated and from a polymeric specie of the hydrophilic polymeric component so as to initiate and promote the cross-linkage of the monomer to the surface and of the monomer or a propagating monomer chain to a polymeric specie of the polymeric component, and a suitable solvent to give the formulation a desired viscosity.

8 Claims, 4 Drawing Sheets

OTHER PUBLICATIONS

Nakayama & Matsuda, "Surface Fixation of Poly (Ethylene Glycol) via Photodimerization of Cinnamate Group," Journal of Polymer Science: Part A: Polymer Chemistry, vol. 31, 3299-3305 (1993).

Macromolecules, vol. 29, No. 9, pp. 3309-3311 (1996).

Yang & Ranby, "Bulk Surface Photgrafting Process and It's Application. III. Photolamination of Polymer Films," J. Appl. Polymer Sciences, 63, 1723-1732, 1997.

Yang & Ranby, "Bulk Surface Photgrafting Process and It's Application. II. Principle Factors Affecting Surface Photografting" J. Appl. Polymer Sciences, 62, 545-555, (1996).

Yang & Ranby, "Bulk Surface Photgrafting Process and It's Application. I. Reactions and Kinetics" J. Appl. Polymer Sciences, 62, 553-543, (1996).

Ciba® IRGACURE® 184 Photoinitiator, Ciba Specialty Chemicals, Inc., Edition Jul. 28, 1999, Basle, p. 1-2.

* cited by examiner

COATING FOR BIOMEDICAL DEVICES

The present invention relates to a coating for biomedical devices and in particular to such a coating which facilitates the passage of the coated device through a body cavity or vessel.

Medical devices are commonly composed of plastic materials or metals. Generally the surfaces of these materials are hydrophobic, and thus tend to be 'non-slippery' and likely to damage tissue during the insertion, positioning and removal of the device, resulting in the possible delay in the recovery of the patient. In recent times this consideration has become an important requirement in the manufacture of biomedical devices.

The introduction and removal of a catheter during an angioplasty procedure involves sliding a catheter through a narrow and tortuous body vessel. It is therefore of great advantage that the friction between the catheter surface and contact tissue be minimised.

An effective way to reduce the friction between the surface of a biomedical device and the body area into which it is introduced is through the use of low friction materials and/or coatings, such as PTFE, glycerine or silicone fluids. However these and similar coatings may present problems to the physician before and during insertion by making the device difficult to handle. It is preferable that the coating would only become slippery following insertion of the device into the patient's body. Such coatings are known and are commonly referred to as lubricious hydrophilic coatings or LHC's, and only become slippery when they come into contact with aqueous environments such as bodily fluids.

These coatings are applied to the medical device by the attachment of hydrophilic polymer chains to the surface. One class of such coatings comprise hydrophilic polymers that possess reactive end groups that can directly attach or graft onto the surface of the device.

U.S. Pat. No. 4,100,309 describes a method for producing a flexible LHC by blending a hydrophilic polymer with a polyurethane binder. U.S. Pat. No. 5,776,611 employs isocyanate chemistry to produce cross-linked hydrogels on the surfaces of devices. Both coatings may be applied to metallic or polymeric substrates. U.S. Pat. No. 5,001,009 describes the preparation of a coating by blending polyvinylpyrrolidone and cellulose esters. The coating can be cast from solution onto biomedical devices and implants such as catheters. In all of these coating systems elevated temperature and aggressive solvents or surface pretreatment are necessary to effect attachment of the coating to the device.

Amiji and Park, ACS Symp. Ser. (1994), 540, pp. 135-146 describe a poly(ethyleneoxide) formulation tipped on one end with an isocyanate group for grafting to a polyurethane catheter surface. Freij-Larsson and Wessien, Journal of Applied Polymer Sciences, (1993) 50, pp. 345-352, reported similar findings using various substrates. Fujimoto et al., J. Polymer Science, Polymer Chemistry Edition, (1993) 31, pp. 1035-1043, describe an ozone pretreatment to produce a hydrophilic layer grafted onto pellethane. In their technique they suggested the use of ozone to pre-treat the substrate in order to produce sites for grafting of acrylamide, which they then polymerised in situ. However in all cases high temperatures were required to bring about the reaction and this possibly causes damage to the substrate.

Another known technique involves the mixing of a hydrophilic polymer and a supporting polymer. This formulation is then applied to the surface of the medical device with the use of a common solvent. The hydrophilic component produces the lubricious coating while the stabilising polymer anchors the soluble polymer through molecular entanglements. This technique is currently used in many commercially available coating formulations including those manufactured and distributed by Hydromer, STS, and Surmodics.

The use of hydrogels as LHC's is also known. Such coatings do not require any anchoring or stabilising component as they are self stabilised through cross-links.

In order to minimise the heating times and temperatures involved in curing LHC's, methods have been developed which use UV radiation to produce such coatings which do not require excessive heating of the substrate, as the reactions rely on low temperature radiation. U.S. Pat. No. 6,110,483 discloses a UV curable coating system which has a high degree of flexibility, consisting of a hydrophilic polymer, a stabilising polymer and an active agent. Such a system avoids the necessity of high cure temperatures to bring about the reaction, but it still requires the use of aggressive solvents. Furthermore, there is a need for several dipping cycles and drying temperatures of at least 50° C. to remove the solvents following the reaction.

U.S. Pat. No. 6,077,698 discloses a chemical linking agent for attaching (any of a number of) many different materials to a surface. The linking agent comprises an at least di-functional photo active compound and at least one charged group to enhance water solubility. A surface is coated with the material by forming an aqueous mixture of the material and linking agent and activating the photoreactive groups to cross-link the material to the surface.

U.S. Pat. No. 5,702,754 discloses a coating comprising polyfunctional crosslinking agent "sandwiched" covalently between a substrate and a hydrophilic polymer having organic acid functional groups.

U.S. Pat. No. 4,979,959 is directed to a method of improving the biocompatibility of a surface by coating it with a linking moiety of structure A-X-B, in which A is a photochemically reactive group capable of bonding covalently to a solid surface, B represents a different reactive group capable of forming a covalent bond to a biocompatible agent and X represents a relatively inert skeletal moiety joining groups A and B.

In U.S. Pat. No. 4,835,003, it is disclosed that a PVP coating having a high molecular weight of at least 800,000 d provides improved lubricating characteristics.

WO 01/17575 discloses a method of coating a substrate by initiating a graft polymerisation reaction on the substrate to generate reactive radical sites on the surface and contacting the substrate with one or more monomers in a medium having different hydrophilicity from the substrate to graft the monomer onto the substrate.

U.S. Pat. No. 6,340,465 discloses a stable, lubricious, biocompatible coating composition comprising a coupling agent, a polyfunctional polymer and at least one biocompatible agent, wherein the coupling agent and the polymer interact to form a three-dimensional crosslinking network which can entrap the biocompatible agent. The polyfunctional polymer disclosed has two or more functionalities. The biocompatible agent may be an antithrombotic agent and in one embodiment, the biocompatible agent is a hydrophilic polymer selected from the group consisting of PVP, PVP/vinyl acetate copolymer and polyethylene oxide.

The present invention seeks to provide a method of coating a medical device which provides a reliable, durable hydrophilic coating for the device.

Accordingly, the present invention provides a coating formulation for a substrate having abstractable hydrogen radicals, the formulation including a hydrophilic polymeric component comprising at least two polymeric species of differing molecular weights, an unsaturated hydrophilic monomer capable of free-radical polymerisation in the presence of a radical and a UV activatable compound capable of abstracting hydrogen radicals from the surface to be coated and from a polymeric specie of the hydrophilic polymeric component so as to initiate and promote the cross-linkage of the monomer to the surface and of the monomer or a propagating monomer chain to a polymeric specie of the polymeric component, and a suitable solvent to give the formulation a desired viscosity.

Preferably, the unsaturated hydrophilic monomer has at least two acrylate functional groups. The at least two polymeric species may include different functional groups. For example, the species may comprise chemically different polymers. The polymeric species may comprise straight chain or branched chain polymers. Ideally, at least one polymeric species comprises a relatively lower molecular weight polymer and at least one polymeric species comprises a relatively higher molecular weight polymer. Molecular weights in the range of 40 kDa to 100 kDa are contemplated for the relatively lower molecular weight polymer and molecular weights in the range of 100 kDa to 1500 kDa are contemplated for the relatively higher molecular weight polymer. Weight ratios of the lower molecular weight polymer to the higher molecular weight polymer of at least about 1-3:1-2 have been found to give coatings with acceptable properties.

In a preferred arrangement, the substrate to be coated comprises a surface of a biomedical device and the formulation's monomeric and polymeric components are biomedically compatible.

The surface to be coated with the formulation of the invention will be one which contains labile hydrogen atoms available for abstraction. Such materials include without limitation nylon-based materials, polyurethanes, polyolefins and polyethyleneterephthalates.

Ideally, the UV activatable compound is selected from any of a group that use a hydrogen abstraction mechanism to initiate polymerisation, including aryl ketones such as benzophenone, xanthone and dichlorobenzophenone. Benzophenone is particularly preferred since it is readily available and inexpensive. A particularly preferred monomer for the coating formulation is acrylic acid, which has the functionality to react both with the substrate and with the polymeric specie on initiation of the hydrogen abstraction mechanism by the UV-activated initiator. Other monomeric species will also be suitable. For example, N-vinyl-2-pyrrolidone would also be a suitable choice and indeed any monomers having unsaturated linkages which produces a final, non-toxic, biocompatible coating will be available for selection. In a preferred arrangement, the polarity of the monomeric species will be a consideration since selection of a suitably polar monomer will enable the monomer to also act as a solvent for the other components of the formulation, thereby reducing the volume of other solvent required, if any.

The invention also provides a coating mixture for a biomedical device which has labile hydrogen radicals available for abstraction, the mixture comprising acrylic acid monomer, at least two hydrophilic polymeric species of differing molecular weight and a UV activatable compound capable of abstracting labile hydrogen radicals from the surface to be coated and from at least one of the polymeric species so that on activation of the UV activatable compound, the components bond to the surface of the biomedical device to coat it with a hydrophilic, interpenetrating matrix of polymers. Ideally, the UV activatable compound comprises benzophenone and the polymeric species comprise polyvinylpyrrolidone.

The system of the invention involves the in situ polymerization of a coating which produces good direct covalent grafting of a hydrophilic polymer to an underlying substrate, for example the surface of a medical device.

By utilizing the monomer as a solvent prior to curing, the use of another solvent or solvents to facilitate the application of the LHC is minimized. UV light is conveniently used to activate, polymerize and crosslink the coating in situ.

The coating formulations of the invention are applicable for coating any surface which permits the abstraction of hydrogen radicals from the substrate by, for example, benzophenone. Any material can be coated if it contains an active hydrogen such as that which would be present in an amino group or an hydroxyl group.

Materials which do not have active such groups may be pre-treated in order to impart the correct functionality to enable them to be coated with a coating formulation of the present invention.

The coating of the invention is useful in particular for coating stent delivery systems, guiding catheters, introducers and other biomedical device. Equally, it is applicable to coating many other materials and any material which has abstractable hydrogen atoms at its surface may be coated using these coatings.

The invention will now be described in more detail with reference to biomedical devices and to the accompanying figures, in which.

The present invention relates to the design and development of a tunable lubricious hydrophilic polymer coating formulations and a method for its direct attachment to substrates, including polymeric substrates.

The coating components include (i) blends of hydrophilic polymeric species of differing chemistry and/or molecular weight, (ii) a liquid monomeric species and (iii) an initiator. Ideally, the polymer blend and monomeric species are readily available, relatively inexpensive and non-toxic materials. Polyvinylpyrrolidone (PVP) is particularly useful as the polymeric species and acrylic acid is particularly useful as the monomeric species. An aryl ketone initiator, such as benzophenone, is particularly suitable as the UV activatable compound for promoting the formation of a coating.

It is believed that when the initiator is activated, the radical generated on the benzophenone can
  (a) initiate chain addition polymerisation of acrylic acid;
  (b) abstract labile hydrogens from nylon and PVP chains to generate radicals to initiate grafting reactions; and
  (c) where a difunctional methacrylate monomer is supplied as a crosslinking agent, initiate polymerisation of this agent leading to a degree of crosslinking.

The radicals generated on the polymer chain can couple with propagating polyacrylic acid chain radicals to graft and terminate the polymerisation, probably giving rise to polyacrylic acid chains of varying chain lengths and probably branches and crosslinks grafted on to the polymer chains. Propagating chains emanating from the polymers can also couple with each other to generate hydrophilic crosslinked structures. Thus the resulting coating will comprise a complex matrix with an interpenetrating network structure.

Figure 1:
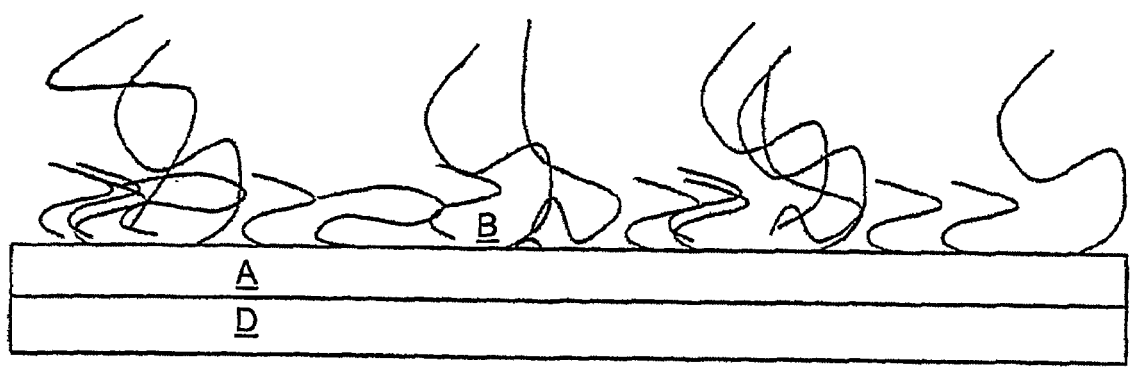
FIG. 1 is a schematic representation of a coating according to the invention applied to a medical device.

The purpose of blending polymers of different chemical species and/or molecular weight is to optimise the hydrophilicity of the coating when wetted, as illustrated in FIG. 1. As shown in that figure, the final coating on the surface of the medical device has polymeric species of differing lengths extending away from it. This provides a means by which water may be trapped between the polymeric species when the surface is wetted, lending it hydrophilic and lubricious characteristics. The final coating will in fact be a chemically heterogeneous system or interpenetrating network, but will nevertheless predominantly comprise of a "layer" A constituted of the former monomer covalently attached to the underlying surface of the medical device D. An outer layer B comprises the different polymeric species covalently linked to the former monomer of layer A. Since the layer B is comprised of polymer of different species and/or molecular weights, the result is that the outer layer comprises a matrix or network of differing chain length or differing degrees of molecular cross-linkage and entanglements of the polymers in the layer. Side reactions further complicate the chemical nature of the coating. For example cross-linking may occur between polymers. All these effects combine to give a coating which can swell on exposure to an aqueous environment to give the coated device a desired lubricity. By altering the components of the system, lubricity, coating strength, durability and hydrophilicity can be adjusted to provide suitable characteristics for a particular device or use. Furthermore, the viscosity of the coating formulation can be modified as desired by choice of the components and solvents.

Typically but not exclusively, the surface to be coated is itself a polymer. The coating is covalently grafted or bonded to it by providing conditions under which the monomeric species binds covalently first to the surface and subsequently to the polymeric species, so that the monomer acts as a bridge or link between the surface and the polymeric material. Differing co-polymeric species of differing length will exist on the surface on termination of the reaction, depending on the number of monomers which polymerise together prior to linkage of a polymeric species to the monomer or polymerised monomer chain, as well as on the chemical nature of the polymer(s) in the mixture.

The purpose of the liquid monomer is to provide a coating which is covalently linked to the underlying surface and on which to covalently attach and anchor the hydrophilic polymeric species, e.g., PVP. In rendering the invention to practise, acrylic acid was used as the liquid monomer which on curing immobilised the PVP on the substrate, as illustrated schematically in FIG. 1.

Figure 2:
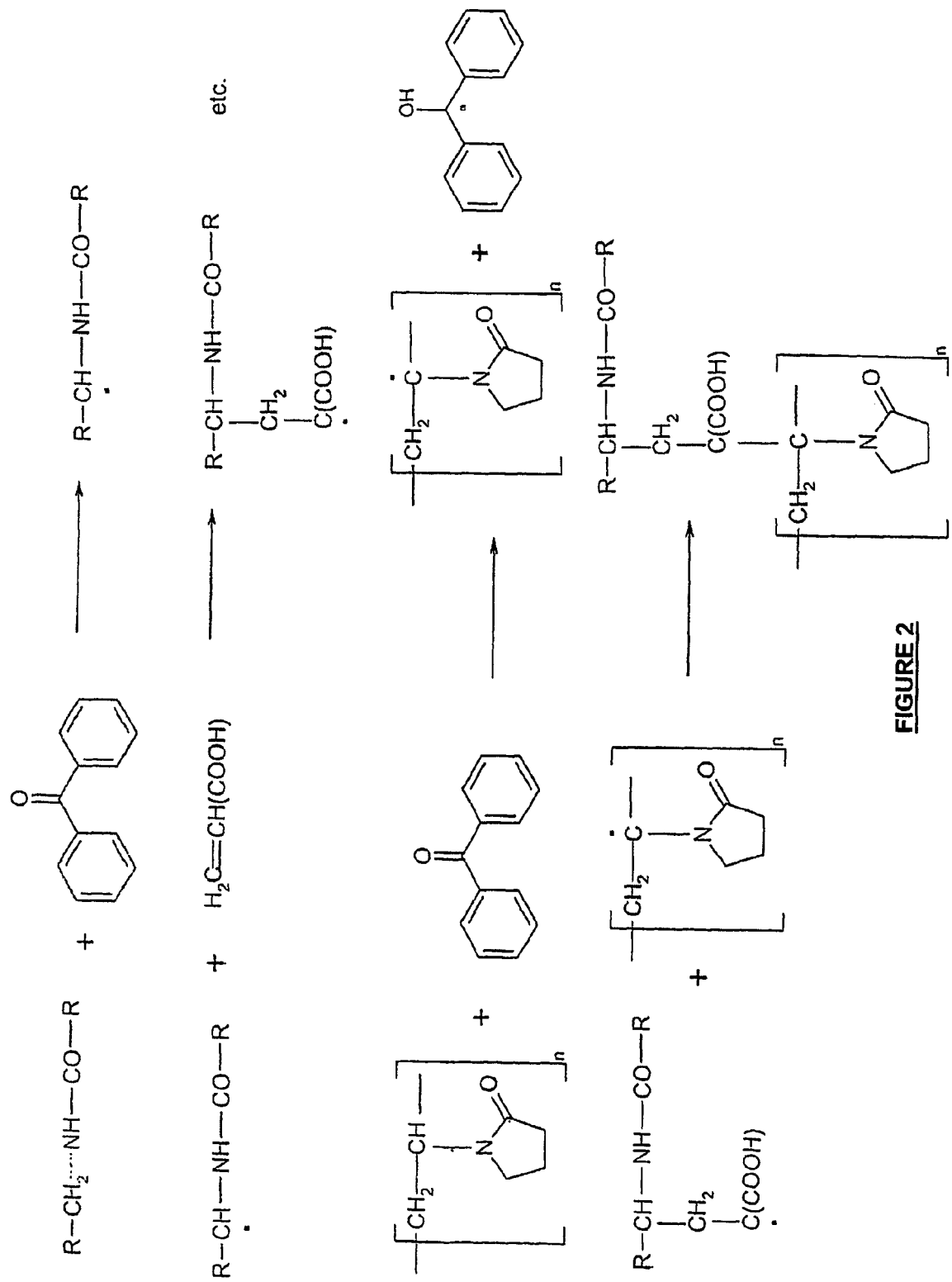
FIG. 2 is a representation of one suggested reaction mechanism for the coating method according to the present invention.

Without wishing to be limited to any particular reaction mechanism, FIG. 2 nevertheless illustrate some of the proposed reactions which are likely to occur in the formation of the coating. Other reactions and side reactions are also likely to occur to differing extents depending on the nature of the materials chosen and the reaction conditions selected. It is believed that the final coating is a complex, interpenetrating network capable of swelling on exposure to an aqueous environment to impart desired lubricious characteristics to the coated article.

Benzophenone is one suitable initiator for the acrylic acid polymerisation. It can also covalently bond the polymer directly to the substrate (i.e. the medical device) polymer through hydrogen abstraction, although in practice this reaction will proceed more slowly and the predominant reaction is that of the covalent linkage of the monomer to the substrate followed by reaction with the polymeric species.

Coatings were prepared by dissolving a desired polyvinylpyrrolidone (PVP) blend in propanol and adding the monomer and initiator (e.g. acrylic acid and benzophenone) in appropriate quantities. The solution was then mixed further before filtration and stored in tinted glass containers.

It is an advantage of the coating of the present invention that the liquid monomer itself contributes as a solvent for the dissolution of the polymeric species, thereby reducing the amount of extraneous solvent in the coating.

The substrate (for example a medical device) is coated by known means. Normally, the area to be coated is cleaned or otherwise treated, e.g., with alcohol, before being immersed in the coating solution. The substrate is then removed from the coating solution and transferred to a curing chamber where the coating is cured by exposure to light or heat, typically UV light, for a period sufficient for the initiator to catalyse the polymerisation. Thereafter, any remaining extraneous solvent is allowed to dry off the surface.

Upon contact with blood, the hydrophilic polymeric coating swells as it absorbs water and creates an aqueous lubricious coating about the coated device, lowering friction between it and the vessel wall and thus reducing damage to the vasculature.

The coating formulation of the invention offers the possibility of using different molecular weights of hydrophilic PVP's or other polymers and the in situ polymerisation of monomer acrylic acid/polymers. The initiator, such as benzophenone, has the dual role when used in excess of abstracting hydrogen radicals from the polymer of the medical device surface and from the monomer, when bound to the surface, to promote polymerisation of further polymers. It can likewise abstract radicals from the PVP chains to initiate grafting reactions.

By blending hydrophilic polymer species of different molecular weights the hydrophilic character of the coating can be modified in order to achieve a desired or optimum lubricity.

The hydrophilic component adheres to the substrate by becoming embedded in an adherent polymer matrix film which is attached through chemical binding to the surface of the substrate.

The direct covalent attachment of the embedding monomer matrix to the substrate by the abstraction of hydrogen from the substrate and the subsequent grafting of the polymer provides a durable and flexible coating.

The hydrophilic coating formulation comprises a number of components which contribute to the application and curing of the coating and the performance of the final product. Use of solvents has been minimised through the use of a monomeric component which prior to curing, acts as a solvent for the other components present and during curing acts as a grafting agent to ensure stability by covalently interlinking to both the surface being coated and to the coating polymer. Preferred monomers include N-vinyl-2-pyrrolidones and acrylic acid and other monomers will also be suitable. Any monomeric compounds containing unsaturated linkages may be used. Monomeric compounds containing active/extractable hydrogen atoms tend to form coatings that are less stable due to lower occurrence of grafting to the substrate. The polarity of the monomer used is also important in relation to its ability to act as an active solvent for the system. Though acting as a solvent prior to cure, during cure the monomer is employed in grafting the coating to the surface of the substrate. The monomers can auto-polymerise to form the coating and predominantly will also graft to the polymeric substances, which serve as viscosity modifiers prior to cure and which enhance lubriciousnes post cure.

A mixture of any suitable monomers may be used.

The UV activatable agent or initiator can be one of many of a group which rely on hydrogen abstraction mechanisms to act as initiators. These include aryl ketones including benzophenone, xanthone and dichlorobenzophenone. As mentioned above, one suggested mechanism for grating is shown schematically in FIG. 2, using benzophenone as the initiator.

Initially the UV excitation of the benzophenone is followed by photoreduction of the substrate (in this case a nylon catheter) via the extraction of the hydrogen atoms. This leaves free radicals on the surface of the substrate which act as sites for covalent bonding of a monomer molecule. Polymerisation of the monomer with itself and/or with the hydrophilic polymer then occurs and the resultant coating is bound to the substrate through covalent bonds.

The use of a polymeric species allows for control of the hydrophilicity (thus lubricity), formulation viscosity and the coating thickness. The use of hydrophilic polymers such as polyvinylpyrrolidone (PVP) and polyethylene-oxide is preferred but others can be used or mixtures of different polymeric species may be used. The presence of active hydrogens along such polymeric materials improves the stability of the coating through the formation of bonds as described above.

Crosslinking agent such as ethylene glycol dimethacrylate (EGDMA) can optionally be incorporated to improve the coating stability and to control swelling of the coating.

Solvents can also be incorporated into the formulation to control the coating thickness. However, solvents such as acetone themselves provide active hydrogens and therefor inhibit the reaction.

The coating formulation of the invention will be suitable for coating any surface which includes susceptible hydrogen atoms, including but not limited to nylon-based materials, polyurethanes, polyolefins, polyethyleneterephthalates and the like. The coating can be applied to the surface by any method known to the skilled person, including dipping, brushing or spraying.

EXAMPLES

Coating formulations were prepared in accordance with Table 1.

TABLE 1

| Example | PVP K90 (Grams) | PVP29/32 (Grams) | Acrylic Acid (Grams) | Benzophenone (Grams) | Propanol (mls) |
|---|---|---|---|---|---|
| 1 | 7.5 | 2.5 | 0.6664 | 0.3328 | 440 |
| 2 | 5 | 5 | 0.6664 | 0.3328 | 440 |

The molecular weight of PVP is often expressed in terms of the Fikentscher K-value that is derived from the solution viscosity as shown in Table 2.

TABLE 2

| Viscosity in H2O cSt (% PVP) | K-Value | Mn (Number Ave) | Mw (Weight Ave) |
|---|---|---|---|
| 7 (20) | 13-19 | 10,000 | 12,000 |
| 25 (20) | 26-34 | 40,000 | 55,000 |
| 50 (10) | 50-62 | 220,000 | 400,000 |
| 400 (10) | 80-100 | 630,000 | 1,280,000 |
| 7000 (10) | 115-125 | 1,450,000 | 2,800,000 |

Table 2 illustrates the relationship between K-Value and the number and weight average molecular weights (From GAF (ISP) Technical Bulletin 2302-203 SM 1290 "PVP polyvinylpyrrolidone polymers 1990".

The PVP was added slowly to the propanol with stirring at room temperature until all the PVP had gone into solution. Next, the acrylic acid and benzophenone were added and stirring was continued until all components were in solution. Thereafter, the solution was filtered providing a stock coating solution. The solution was protected from light during preparation and subsequent storage. The stock solution was filtered. This solution can be stored, protected from light, for up to three weeks.

An article to be coated, such as a nylon catheter, is firstly end-sealed to prevent coating solution from entering into the lumen of the catheter. The sealed shaft is then cleaned by wiping with a solvent such as propanol. The shaft is lowered into the prepared stock coating solution and withdrawn sufficiently slowly to allow excess coating to flow off. The dipped article is held at room temperature for about 3 minutes to allow it to drip and thereafter, it is moved into a UV chamber. Once the shaft has been dipped, great care is taken to avoid touching the surface, thereby damaging the final coating. The UV chamber includes a UV source operating at about 365 nm. Following a residence in the chamber of about 3 minutes, the coating cures and the shaft is withdrawn and allowed to cool for about 3 minutes. At the end of the cooling cycle, any remaining propanol solvent will have evaporated off and the coating is complete and dry. Once the shaft has cooled, it is passed to downstream processing steps which include a visual inspection of the coated surface to ensure its integrity and removal of the sealed tip so that the lumen is once again open.

The coating formulations were used to coat lengths of nylon tubing according to the method described above. The coated lengths were each inspected visually to assess the gross appearance of the coating and its smoothness and integrity. In addition, a manual assessment of the coating was made by rubbing the coated tubing twice between the fingers and assessing the lubricity and durability of the coating of Examples 1 and 2 of Table 1. The results of the visual and manual inspections are set out in Table 3.

TABLE 3

| Example | Feel | $2^{nd}$ Run | Lubricity | Durability | Comments |
|---|---|---|---|---|---|
| 1 | Pass | Pass | 1 | 2 | Feels Good and Lub |
| 2 | Pass | Fail | | | Feels Good and Lub |

Lub = Lubricions

Figure 3:
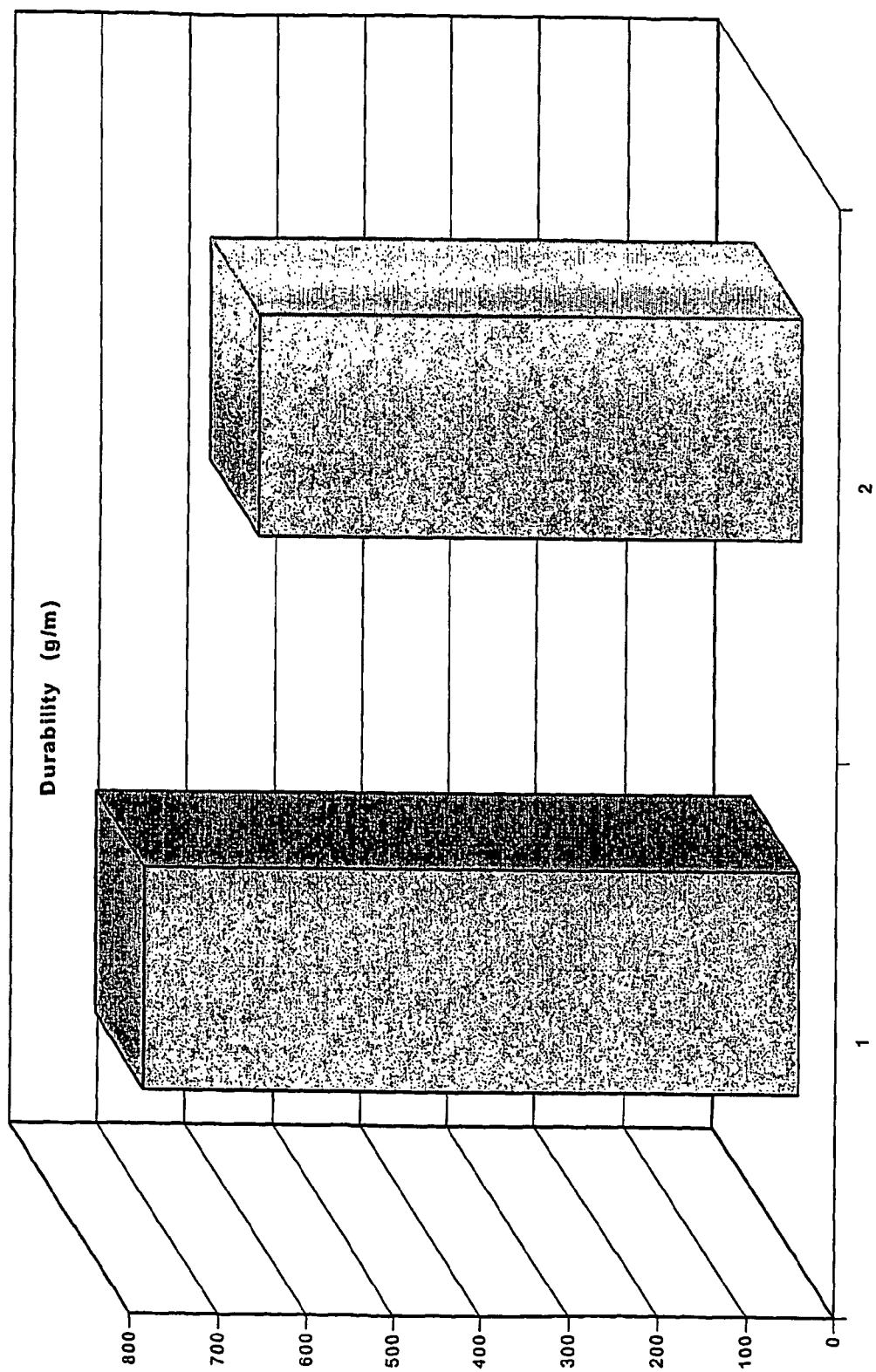
FIGS. 3 and 4 are charts showing results of durability tests and frictional tests carried out on different coatings formulations.
Figure 4:
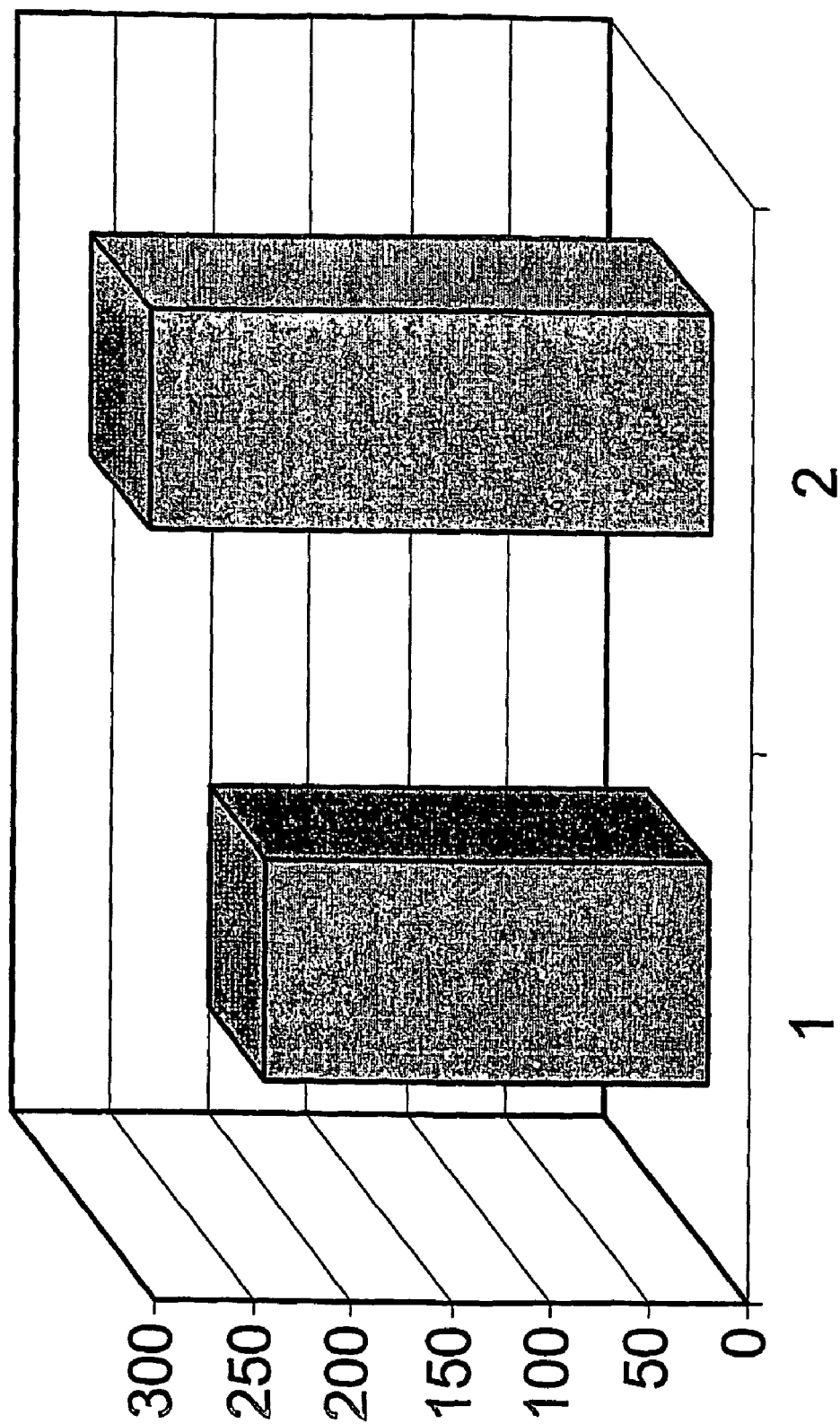

The lubricity characteristics of the coatings were measured using a calibrated test rig set up to measure the initial frictional force in grams exerted as tubing pre-wetted in water at room temperature is drawn through a jaw pair. Durability of the coating was assessed by measuring initial frictional forces over iterative drawings. FIGS. 3 and 4 are respectively plots of the durability and initial frictional forces measured for the different coating formulations and Table 4 details the result of the lubricity and durability studies for Examples 1 and 2.

TABLE 4

| Example | 1st cycle peak (g) | 10th cycle peak (g) | 1st Energy | 10th cycle Energy (g/m) | Durability (g/m) |
|---|---|---|---|---|---|
| 1 | 63.2 | 128.6 | 512.2 | 878.4 | 366.2 |
| 2 | 60.2 | 595.4 | 572.4 | 5111.8 | 3484.4 |

Example 1 was selected as the best performing sample in both frictional durability studies and hand evaluation.

In the preferred embodiment of the invention described above, the two critical components relating to the curing and performance of the coating are the acrylic acid and benzophenone.

The following ranges of these components, based on solutions of 2.156% PVP K90 and 0.7197% PVP K29/32 in isopropanol, are suitable for use in the present invention.

Benzophenone range 0.0088% to 0.01%
Acrylic Acid Range 0.0177143% to 0.02%.

These ranges, which are wt/volume, are also suitable for other solutions of the polymers.

Additions of PVP weight ranged from 0.025% to 25.0%. The molecular weight of the PVP is an important factor due to its effect on the solution viscosity). Molecular weight combinations of low and high molecular weight species are preferred).

Further examples 3 to 13 of formulations suitable for use in the present invention are set the attached Table 5.

TABLE 5

| Example | Polymer A | Polymer B | Ratio | Polymer C | Initiator | Solvent |
|---|---|---|---|---|---|---|
| 1 | PVPa 7.5 g (75% wt) Mw 40 kDa | PVPb 2.5 g (25%) Mw 360 kDa | 3:1 | Acrylic Acid (AA) | Benzephenone (0.0001% wt) | AA Isopropanol 440 mls |
| 2 | PVPa 5.0 g (50%) Mw 40 kDa | PVPb 5.0 g (50%) Mw 360 kDa | 1:1 | Acrylic Acid (AA) | Benzephenone (0.0001% wt) | AA Isopropanol 440 mls |
| 3 | PEO a 6.0 g (60% wt) Mw 100 kDa | PEO b 4.0 g (40% wt) Mw 300 kDa | 3:2 | N-Vinyl 2 Pyrrolidone (NV2P) | Benzephenone (0.1 g) | NV2P Isopropanol 220 mls H20 (dist.) 220 mls |
| 4 | PEO a 6.0 g (60% wt) Mw 40 kDa | PEO b 4.0 g (40% wt) Mw 1500 kDa | 3:2 | N-Vinyl 2 Pyrrolidone (NV2P) | Benzephenone (0.1 g) | NV2P in Isopropanol 220 mls H20 (dist.) 220 mls |
| 5 | PVP 6.0 g (60% wt) Mw 40 kDa | PEO b 4.0 g (40% wt) Mw 100 kDa | 3:2 | N-Vinyl 2 Pyrrolidone (NV2P) | Benzephenone (0.1 g) | NY2P in Isopropanol 220 mls H20 (dist.) 220 mls |
| 6 | PEO a 6.0 g (60% wt) Mw 100 kDa | PEO b 4.0 g (40% wt) Mw 1000 kDa | 3:2 | Methyl methacrylate | Benzephenone (0.1 g) | MMA in Isopropanol 220 mls H20 (dist.) 220 mls |
| 7 | PEO a 6.0 g (60% wt) Mw 100 kDa | PEO b 4.0 g (40% wt) Mw 1000 kDa | 3:2 | Hydroxy ethyl acrylate (HEA) | Benzephenone (0.1 g) | HEA in Isopropanol 220 mls H20 (dist.) 220 mls |
| 8 | PHEMA 6.0 g (60% wt) Mw 100 kDa | PVP 4.0 g (40% wt) Mw 300 kDa | 3:2 | Acrylic acid (AA) | Hydroxy cyclohexyl phenyl ketone (0.1 g) | AA in Isopropanol 440 mls |
| 9 | PVP 6.0 g (60% wt) Mw 40 kDa | PHEMA 4.0 g (40% wt) Mw 100 kDa | 3:2 | Acrylic Acid (AA) | Benzephenone (0.0001% wt) | AA Isopropanol 440 mls |
| 10 | PVP a 6.0 g (60% wt) Mw 40 kDa | PVP b 4.0 g (40% wt) Mw 360 kDa | 3:2 | N-Vinyl 2 Pyrrolidone (NV2P) | Hexamethylene disocyanate (0.0001% wt) | NV2P Isopropanol 440 mls |
| 11 | PVP a 6.0 g (60% wt) Mw 40 kDa | PVP b 4.0 g (40% wt) Mw 360 kDa | 3:2 | Acrylic Acid (AA) | Hydroxy cyclohexyl phenyl ketone (0.1 g) | AA Isopropanol 440 mls |
| 12 | PEO 6.0 g (60% wt) Mw 100 kDa | PHEMA 4.0 g (40% wt) Mw 1000 kDa | 3:2 | Acrylic Acid (AA) | Hydroxy cyclohexyl phenyl ketone (0.1 g) | AA Isopropanol 220 mls H20 (dist.) 220 mls |
| 13 | PVP a 6.0 g (60% wt) Mw 40 kDa | PVP b 4.0 g (40% wt) Mw 360 kDa | 3:2 | N-Vinyl 2 Pyrrolidone (NV2P) | Benzephenone (0.0001% wt) | NV2P Isopropanol 440 mls |

Polymer A: Hydrophilic polymer
Polymer B: Amphiphilic polymer
Polymer C: Hydrophilic monomer
Typical Ratio's Polymer A:Polymer B (50-75%):(25-50%)
PHEMA Poly hydroxy ethyl methacrylate
PVP Polyvinyl methacrylate
PEO Poly ethylene oxide
PU Polyurethane (Hydrophilic/Hydrophobic) species It will of course be understood that the invention is not limited to the specific details herein described, which are given by way of example only and that various alterations and modifications may be made without departing from the scope of the invention as defined in the appended claims.

The invention claimed is:

1. A durable hydrophilic biocompatible coating formulation for a medical device having abstractable hydrogen radicals, the formulation including a hydrophilic polymeric component comprising at least two polymeric species of differing molecular weights, an unsaturated hydrophilic monomer capable of free-radical polymerisation in the presence of a radical and a UV activatable compound capable of abstracting hydrogen radicals from the surface to be coated and from a polymeric species of the hydrophilic polymeric component so as to initiate and promote the cross-linkage of the monomer to the surface and of the monomer or a propagating monomer chain to a polymeric species of the polymeric component, and a suitable solvent, wherein said formulation is suitable for coating on an implantable biomedical device with only one curing step, wherein at least one polymeric species comprises a relatively lower molecular weight polymer and at least one polymeric species comprises a relatively higher molecular weight polymer, and wherein the ratio of lower molecular weight polymer to higher molecular weight polymer is between about 1:3 and 1:2, and wherein the relatively lower molecular weight polymer has molecular weight in the range of 40 kDa to 100 kDa and the relatively higher molecular weight polymer has a molecular weight in the range of 100 kDa to 1500 kDa, wherein the coating comprises a first layer comprising the monomer capable of covalently attaching to the surface of the biomedical device and a second layer comprising a polymer that is covalently linked to the monomer layer.

2. A biocompatible coating formulation as in claim 1, wherein the unsaturated hydrophilic monomer has at least two acrylate functional groups.

3. A biocompatible coating formulation as in claim 1, wherein the at least two polymeric species include different functional groups.

4. A biocompatible coating formulation as in claim 1, wherein the at least two polymeric species comprise chemically different polymers.

5. A biocompatible coating formulation as in claim 1, wherein the at least two polymeric species comprise straight chain or branched chain polymers.

6. A biocompatible coating formulation as in claim 1, wherein the UV activatable compound is selected from any of a group that use a hydrogen abstraction mechanism to initiate polymerisation, including aryl ketones selected from the group consisting of benzophenone, xanthone and dichlorobenzophenone.

7. A biocompatible coating formulation as in claim 6, wherein the UV activatable compound is benzophenone.

8. A biocompatible coating formulation as in any one of claims 1, 5, and 6-7, wherein the monomer for the coating formulation is acrylic acid, which has the functionality to react both with the substrate and with the polymeric on initiation of the hydrogen abstraction mechanism by the UV activatable compound.

* * * * *